(12) United States Patent
Pommereu

(10) Patent No.: US 9,463,279 B2
(45) Date of Patent: Oct. 11, 2016

(54) MEDICAL DEVICE AND METHOD OF ASSEMBLY

(75) Inventor: Christian Pommereu, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 660 days.

(21) Appl. No.: 13/516,120

(22) PCT Filed: Dec. 16, 2010

(86) PCT No.: PCT/EP2010/069903
§ 371 (c)(1),
(2), (4) Date: Sep. 27, 2012

(87) PCT Pub. No.: WO2011/080092
PCT Pub. Date: Jul. 7, 2011

(65) Prior Publication Data
US 2013/0012871 A1 Jan. 10, 2013

(30) Foreign Application Priority Data

Dec. 17, 2009 (EP) .................................. 09179623

(51) Int. Cl.
*A61M 5/50* (2006.01)
*B23P 17/04* (2006.01)
(Continued)

(52) U.S. Cl.
CPC *A61M 5/24* (2013.01); *G06T 1/00* (2013.01); *A61M 5/3146* (2013.01);
(Continued)

(58) Field of Classification Search
CPC ............... A61M 5/24; A61M 5/3146; A61M 5/31551; A61M 5/31561; A61M 5/31575; A61M 5/31585; G06T 1/00; Y10T 29/49826; Y10T 29/49769

USPC .................................. 604/207–211; 116/200
See application file for complete search history.

(56) References Cited

U.S. PATENT DOCUMENTS 5,464,396 A    11/1995  Barta et al.
7,462,166 B2 * 12/2008  Cowan ............. A61M 5/14546
                                                        604/131
(Continued)

FOREIGN PATENT DOCUMENTS

EP    1640421 A1    3/2006
FR    2909095 A1    5/2008
(Continued)

OTHER PUBLICATIONS

Form PCT/IPEA/416, Notification of Transmittal of the International Preliminary Report on Patentability.

*Primary Examiner* — Theodore Stigell
(74) *Attorney, Agent, or Firm* — McDonnell Boehnen Hulbert & Berghoff LLP

(57) ABSTRACT

The present invention relates to a medical device for administering a medicinal product to a patient comprising at least one component (2, 8, 10, 12, 14, 15, 16, 17, 18, 20, 22, 24, 26, 28) comprising a material having an additive embedded therein, wherein the additive is adapted to provide a visually perceptible signal when exposed to electromagnetic radiation. The invention is particularly intended for drug delivery devices, such as e.g. of pen-type injectors. With the visually perceptible signal embedded in the at least one component, visually controlled assembly of such devices can be improved. Additionally the invention provides an effective means antagonize counterfeiting of drugs and of medical devices.

11 Claims, 1 Drawing Sheet

(51) Int. Cl.
*A61M 5/24* (2006.01)
*G06T 1/00* (2006.01)
A61M 5/31 (2006.01)
A61M 5/315 (2006.01)

(52) U.S. Cl.
CPC ..... *A61M 5/31551* (2013.01); *A61M 5/31561* (2013.01); *A61M 5/31575* (2013.01); *A61M 5/31585* (2013.01); *Y10T 29/49769* (2015.01); *Y10T 29/49826* (2015.01)

(56) References Cited

U.S. PATENT DOCUMENTS

| | | | |
|---|---|---|---|
| 2003/0018353 A1* | 1/2003 | Yang et al. | 606/194 |
| 2004/0019333 A1* | 1/2004 | Graf et al. | 604/207 |
| 2006/0222702 A1 | 10/2006 | Barreto et al. | |
| 2009/0209695 A1 | 8/2009 | Yu et al. | |
| 2009/0312713 A1 | 12/2009 | Greutert et al. | |

FOREIGN PATENT DOCUMENTS

| | | |
|---|---|---|
| GB | 2243578 A | 11/1991 |
| JP | 07155375 A | 6/1995 |
| JP | 2005506852 A | 3/2005 |
| JP | 2008515471 A | 5/2008 |
| JP | 2008539136 A | 11/2008 |
| JP | 2009536562 A | 10/2009 |
| WO | 02056934 A2 | 7/2002 |
| WO | 2006037434 A1 | 4/2006 |
| WO | 2006117692 A1 | 11/2006 |

* cited by examiner

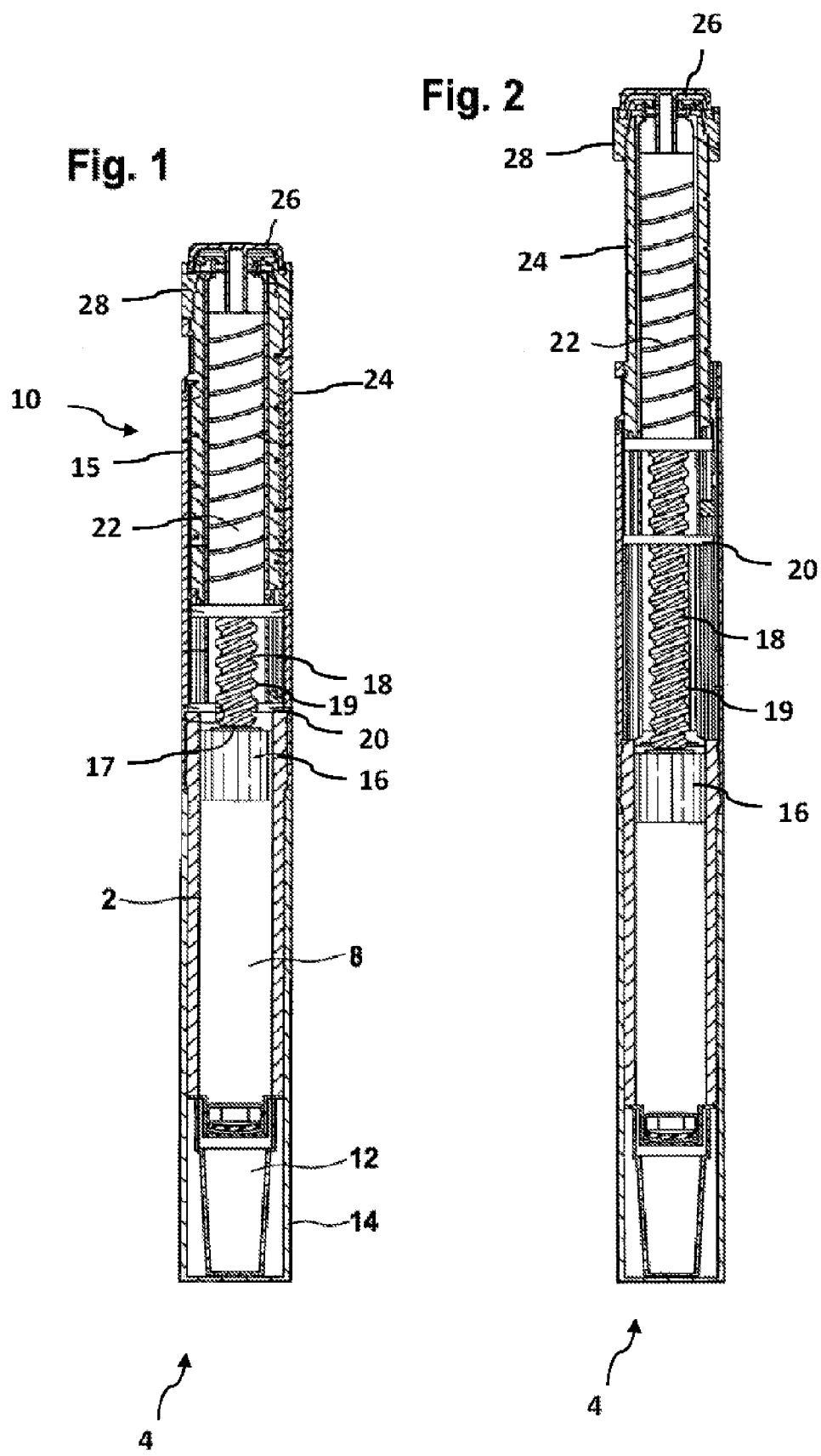

MEDICAL DEVICE AND METHOD OF ASSEMBLY

CROSS REFERENCE TO RELATED APPLICATIONS

The present application is a 35 U.S.C. 371 National Application of PCT/EP2010/069903 filed Dec. 16, 2010, which claims priority to European Patent Application No. 09179623.5 filed Dec. 17, 2009, the entire contents of which are incorporated entirely herein by reference.

The present invention relates to medical devices and in particular to drug delivery devices such as pen-type injectors. Moreover, the invention relates to a method of assembly as well as to a method of labelling medical devices, in particular of drug delivery devices.

BACKGROUND AND PRIOR ART

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Pen-type injectors of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

In particular with disposable devices manufacturing and production costs have to be kept at a minimum. Hence, drug delivery devices, such as pen-type injectors are nowadays typically manufactured by way of a fully automatic production.

Due to inevitable tolerances in the outer dimensions of the components of such devices and due to tolerances in the assembly procedure itself, presence, position as well as orientation of particular components of such devices have to be visually controlled and inspected in order to allow for a precise assembly that fulfils given quality standards for such medical devices.

Visual inspection and manufacturing control is typically conducted by way of automatic image acquisition and digital processing of acquired images. This method however requires that the components to be visually inspected provide sufficient contrast with respect to a surrounding environment. This requirement limits the range of materials and colours adequate for respective device components.

Additionally, an increase of counterfeited drug delivery devices and drugs has been recently observed that are typically of substandard quality. Counterfeited drugs and devices carry a significant risk to health and may further damage reputation of the original equipment and drug manufacturer.

Another problem has been observed with drugs and medical devices featuring an exceeded expiration date. The medical device but also respective medical substances, such as drugs, should no longer be used once their expiration date has been reached. Patients using drugs and medical devices on a rather irregular but long-term time schedule, may therefore be exposed to a certain risk of health if not being explicitly and timely informed about an approaching expiration date.

Objects of the Invention

In view of the above-mentioned deficiencies, it is an object of the present invention, to provide a means for facilitating and for optimizing a mass production process for medical devices, in particular for pen-type injectors. It is a further object of the present invention to antagonize counterfeiting of drugs and respective medical devices. Additionally, the invention focuses on improved labelling and distinguishing of drugs and respective devices which due to an exceed of the respective expiration date should no longer be used or administered.

SUMMARY OF THE INVENTION

The present invention provides a medical device for administering a medicinal product to a patient. The medical device comprises at least one component that comprises a material having an additive embedded therein. The additive is preferably embedded in the bulk of the at least one component. Said additive is furthermore adapted to provide a visually perceptible signal when exposed to electromagnetic radiation. Preferably, the additive responds to a predefined spectrum of electromagnetic radiation in a different way compared to the surrounding material of the component. By exposing the at least component to a respective spectrum of electromagnetic radiation, the embedded additive inside said component will provide a visually perceptible signal that can be used in a manifold of different ways and for respective purposes.

By embedding the additive in the bulk of the at least one component of the medical device, the respective component does not require additional surface treatment. Also, the component maintains its visual properties and its response to electromagnetic radiation even if it becomes subject to wear or abrasion if used for a long time.

It is of particular benefit for the present invention, that the additive is embedded in the bulk of the at least one component. Instead of providing the component with an additive-containing coating, which requires supplemental steps in a respective production process, the invention advantageously characterises in that the visually perceptible additive is substantially homogeneously distributed in the bulk of the component.

On the one hand, only the raw material the component is made of has to be modified appropriately. Subsequent steps, e.g. of assembly or after-treatment of said component can thus remain unaltered in an existing process of mass production.

On the other hand, by embedding an additive into the at least one component, said component always provides a rather constant visually perceptible signal, even when the component is subject to abrasion or wear. Also and in comparison with a coating, the visually perceptible reply of the material to a selected electromagnetic radiation becomes an inherent property of said component.

According to a first preferred embodiment, the material of the at least one component comprises an injection molded thermoplastic material, wherein the additive comprises at least one dye, e.g. in form of pigments being substantially homogeneously distributed in the material. Preferably, the respective dye is mixed with the thermoplastic raw material, which may for instance be provided in granular form.

Mixing the thermoplastic raw material together with the at least one dye provides a composition as a starting material, which after completion of a thermoplastic injection moulding process ends up in a thermoplastic component of a medical device having at least one respective dye substantially homogenously embedded and distributed therein.

According to a further preferred embodiment, the additive may comprise colour pigments, by way of which the colour of the respective component is modified in such a way, that image acquisition and image processing of such a component within a fully automatic production can be is sufficiently conducted. Hence, the embedded dye provides sufficient contrast, which at least allows to determine presence, position and/or orientation of the respective component.

In a further preferred embodiment, the additive is only sensitive to a particular range of electromagnetic radiation. Also, the additive may react in different ways when exposed to electromagnetic radiation of particular wavelength. For instance, the additive might be fluorescent in response to a first spectral range of the electromagnetic radiation. Typically, the additive may provide a fluorescent response to an excitation provided by electromagnetic radiation in the UV-spectral range.

With fluorescence, the respective additive or dye may be adapted to absorb photons in the ultraviolet spectral range and may emit photons in the visible spectral range. In this way, visualization of the at least component can be effectively conducted by exposing said component to non-visible radiation, such as electromagnetic radiation in the UV-spectral range, while a camera or image acquisition system is adapted to monitor position and/or orientation of the component by detecting light in the respective visible spectral range.

Appropriate additives belong for instance to the group of 2,2'-(2,5.-Thiophenediyl)-bis[5-tert-butylbenzoxazole]. Additives of this type can be promptly used in polymers and adhesives and do not represent a risk of health for a patient.

In another embodiment, the additive is photochromic with respect to a second spectral range of the electromagnetic radiation. Hence, the additive undergoes a reversible or irreversible photochemical reaction when exposed to electromagnetic radiation within a pre-defined radiation spectrum. Due to the photochemical reaction inherent to the photochromic additive, an absorption band in the visible part of the electromagnetic spectrum of said material changes in intensity and/or in wavelength. The additive might become subject to a pericyclic reaction, to cis-trans isomerisations, intramolecular hydrogen transfer, intramolecular group transfers, dissociation processes and electron transfers. The additive can therefore belong to various different classes: triarylmethanes, stilbenes, azastilbenes, nitrones, fulgides, spiropyrans, naphthopyrans, spiro-oxazines, quinones and others.

Embedding of photochromic additives in the bulk of a peripheral component of a medical device is beneficial in many aspects. The photochromic additive provides a component-inherent labelling, e.g. if the device has been exposed to hazardous radiation. Additionally, the photochromic additive typically modifies the optical transmission and absorption properties of a respective component. Providing for instance an at least partially transparent cartridge holder with a photochromic additive, exposure with electromagnetic radiation then leads to a respective increase in absorption of radiation. In this way, the cartridge comprising a medicinal substance can be effectively protected against continuing exposure of radiation.

In another embodiment, the additive embedded in the at least one component is substantially absorptive or reflective with respect to a third spectral range of the electromagnetic radiation. For instance, the additive may be substantially opaque with respect to high energetic electromagnetic radiation, such as X-rays. In this way it is even conceivable, to make us of an X-ray opaque additive in order to visualise the at least one component of the medical device when exposed to X-rays. For instance by way of X-ray inspection an effective anti-counterfeiting means can be implemented, which only under appropriate test conditions provides a requested X-ray opaque pattern to be visualised.

By making use of electromagnetic radiation in the X-ray spectral range, the at least one component can furthermore arranged almost anywhere at the outer circumference or even inside the medical device. Since residual components of such devices are substantially transparent for the electromagnetic radiation of choice, which is normally the case for conventional thermoplastic materials, presence, position and/or orientation of said X-ray opaque component can be inspected in situ.

According to another preferred embodiment of the invention, the first, second, and/or third spectral ranges comprise a spectral width (Full Width at Half Maximum (FWHM)) of less than 100 nm, preferably less than 50 nm, most preferably less than 10 nm or even less than 5 nm. By decreasing the bandwidth, in which the additive provides a response to a respective electromagnetic stimulation, an effective anti-counterfeiting means can be substantially improved. Especially in keeping secret the wavelength of choice, to which the additive provides a visually perceptible or an at least detectable electromagnetic signal, counterfeiting of such devices becomes more difficult because a counterfeiter may not be aware, that the original part provides a particular visually or optically detectable response only under specific and secret-kept ambient conditions.

In another embodiment, the first, second and/or third spectral ranges are within the infrared-, visible-, UV- or X-ray spectral range. Depending on whether the visually perceptible signal is to be used as an anti-counterfeiting means or as a means for facilitating assembly of the device in e.g. an automated mass production, the inspection wavelength and a corresponding additive can be selected accordingly.

Additionally, it is conceivable for the present invention, to make use of a multiplicity of different additives, wherein for instance a first additive provides a visual response to UV-exposure while a second additive is opaque and absorptive with respect to X-rays. While a first additive might be useful for an automatic device assembly, the second additive may be adapted to provide an anti-counterfeiting feature.

In another embodiment, the additive irreversibly changes at least one of its visually perceptible properties once it has been exposed to a predetermined amount of radiation of a given spectral range. For instance, the additive can be of irreversible photochromic type and a photochemical reaction may be triggered as soon as energy deposited by radiation within a specific spectral range exceeds a pre-defined threshold.

By means of an irreversible change in the additive's visually perceptible properties, the medical device and/or a drug to be delivered by such devices can be labelled as having exceeded its expiration date. In this way, a user or a patient can be provided with important information, that usage of such medical devices or drugs may involve a risk to health.

Further and according to another preferred embodiment, the material is configured as a lubricant. Hence, a component of the medical device may be provided with a lubricant in the process of assembly. The lubricant may comprise the additive and may therefore allow to visualize the respective component when exposed to the selected radiation.

It is even conceivable, that the component being enriched with the additive is a lubricant member, which serves to provide a lubricant effect to other functional components of a medical device, in particular of a drug delivery device. By embedding the additive in the bulk of a lubricant member, the position and/or the presence of the lubricant member can be optically controlled during a mass production or mass assembly process of the device.

In this context, also a receptacle or a through opening of a particular device component, e.g. a number sleeve of the drive mechanism of a drug delivery device, can be at least partially filled with a lubricating substance having an embedded additive. When appropriately illuminated in the course of an automated production process, the presence, a correct position and/or deviations from a pre-defined position of the respective device component, e.g. the number sleeve can be controlled in an all-optical way.

In a further aspect, the invention also provides a medical device configured as drug delivery device, wherein the device comprises a housing, a drive mechanism and a cartridge holder which is adapted to receive a cartridge being filled with a medicinal product. Said cartridge is typically configured as a vial or a carpule and has a piston slidably disposed therein. The drive mechanism of the medical device is further to be operably engaged with the piston of the cartridge. Typically, a piston rod of the drive mechanism operably engages with the cartridge's piston for dispensing of a dose of the medicinal product.

According to the present invention, the housing, the drive mechanism, the piston rod, the cartridge holder and/or a separately added lubricant or other individual components of the device can designed as the at least one component in the sense of the present invention having the additive embedded therein. In this way, any one or several of the components of the medical device may comprise an embedded additive, which allows to improve visualization of the respective component's presence, position or orientation e.g. in a fully automatic production process.

By making use of an appropriate exposure system, the respective components and parts of the medical device may provide enhanced contrast and may be better illustrated and detected by e.g. camera-based detection systems or by the human eye. In this way, reliability and failure safety of an assembly process can be enhanced and the production efficiency of such assembly lines can be optimized.

Generally, the medical device according to the present invention may refer to any medical device, which is adapted to deliver or to administer medicinal fluids to a patient. Hence, the medical device is preferably designed as a drug delivery device, preferably as an injection device or as an inhaler. Generally, the invention can be universally applied to pen-type injection systems, syringes, inhalers, to vials, cartridges, tubes and containers and other components of such devices.

In another aspect, the invention also refers to a method of assembly of a drug delivery device adapted for dispensing of a dose of a medicinal product. The drug delivery device, e.g. a pen-type injector, comprises at least one or several of the following components: housing, drive mechanism and/or a cartridge holder adapted to receive a cartridge filled with the medicinal product and comprising a piston slidably disposed therein. The drive mechanism is to be operably engaged with the piston of the cartridge by means of a piston rod for dispensing of a single or multiple doses of the medicinal product. The method of assembly according to the present invention comprises the steps of embedding of at least one additive in the bulk of at least one of said components, wherein the additive is adapted to provide a visually perceptible signal when exposed to electromagnetic radiation of a pre-defined wavelength.

Next, the component is exposed to said electromagnetic radiation, e.g. within a fully automatic production procedure. Due to exposure with said electromagnetic radiation, the additive provides a visual or an at least optically detectable response, which is detected accordingly for determining of its presence, its absolute relative position and/or its orientation. By having knowledge of the presence, relative or absolute position and/or orientation of said component, the at least one component or a sub-assembly of the drug delivery device is assembled with another component or with another sub-assembly of the drug delivery device.

Preferably, the position or orientation of the at least one component is determined by means of processing of an image, in which the component is illustrated contrast enhanced. If for instance, the additive is fluorescent when exposed to UV-light, by making use of appropriate filters in an imaging system, the presence, position and/or orientation of said component can be precisely and easily determined by an appropriate image acquisition and image processing system.

In another independent aspect, the invention further provides a method of labelling of a medicinal device with a certificate of authenticity. Said method comprises the steps of embedding of an additive in the bulk of at least one component of the medical device, wherein the additive is adapted to provide a visually perceptible signal when exposed to electromagnetic radiation of a predefined, selected and limited spectral range. In order to check or to control whether the medical device is a genuine part, either the entire device or at least its particular component is exposed to electromagnetic radiation of said spectral range.

By subsequently detecting and/or analyzing electromagnetic radiation reflected, transmitted or scattered by said component, it can be precisely determined, whether the component and/or the entire medical device is counterfeited or not. In this context it is of further benefit, when the additive is only responsive to a particular small band of the electromagnetic spectrum. Preferably, the additive is only responsive to a spectral range having a width (Full Width at Half Maximum (FWHM)) of less than 100 nm, preferably less than 50 nm, most preferably less than 10 or less than 5 nm.

Furthermore, by keeping secret the spectral range, to which the additive is responsive, said anti-counterfeiting means can even be improved. Moreover, when making use of exposure electromagnetic radiation in the invisible spectral range, such as by making use of UV-radiation or even by X-rays, the optical response of a particular component can even be examined without the necessity of disassembling the entire device. This is of particular benefit, when the component provided with said additive is arranged inside the medical device.

In another further independent aspect, the invention also refers to a method of visualizing an unusability of a medical device, wherein in a first step an additive is selected, that is adapted to change at least one visually perceptible property when exposed to electromagnetic radiation of a predefined wavelength for at least a predefined period of time. Thereafter, the appropriate additive is embedded in the bulk of at least one component of the medical device. Preferably, said additive is mixed with a raw material being subject to a subsequent forming process, e.g. such as injection molding. Preferably, said additive is adapted to undergo a photochemical reaction once exposed to a predefined amount of radiation energy.

Deposition of a predefined amount of radiation energy is typically an indicator, that a respective device or a respective container already exceeded its expiration date. A change in at least one optical property of the additive is therefore an indicator, that the medical device and/or its medicinal product should be no longer used or administered to a patient. Typically, the component of the medical device may at least partially change its colour, thereby indicating to a user, that its expiration date has been exceeded.

Furthermore it has to be mentioned, that a visually perceptible signal according to present invention refers to any electromagnetic signal being detectable by the human eye or be means of detectors being even sensitive in a spectral range outside the visual spectrum. Moreover, the visually perceptible signal can be based on absorption-, reflection-, scattering-, excitation and emission processes provided by the additive embedded in the at least one component.

Additionally it is to be mentioned, that only part of a component of a medical device may become subject to an embedding of an additive. For instance, a selected component of a drug delivery device may be configured as a 2-component or 2K-injection molded component, wherein only one of these components is provides with said additive.

It will be apparent to those skilled in the pertinent art that various modifications and variations can be made to the present invention without departing from its spirit and scope. Further, it is to be noted, that any reference signs used in the appended claims are not to be construed as limiting the scope of the present invention. It is further to be noted, that the present invention can be universally applied and implemented with numerous medical devices as well as to different methods focussing on assembly, labelling and/or visualizing an unusability of medical devices, and in particular of drug delivery devices, such as pen-type injectors.

BRIEF DESCRIPTION OF THE DRAWINGS

Without limitation, the present invention will be explained in greater detail below in connection with preferred embodiments and with reference to the drawings in which:

FIG. 1 shows a drug delivery device in cross section in an initial configuration and FIG. 2 illustrates the drug delivery device according to FIG. 1 prior dose dispensing.

DETAILED DESCRIPTION

The drug delivery device 4 as illustrated in FIGS. 1 and 2 comprises a cartridge holder 2 that serves to house and to receive a cartridge 8 filled with a medicinal product to be dispensed by the drive mechanism 10 of the drug delivery device 4. The cartridge 8 comprises at its upper, hence proximal end section a piston 16 moveably disposed in said cartridge 8. A removable cap 12 is releasably retained at a lower, distal end of the cartridge holder 2. In use, said cap 12 can be replaced by a suitable piercing element, such an injection needle, cannula or the like for dispensing and administering the liquid drug to a patient.

The entire cartridge holder 2 is further covered by another replaceable cap 14. Preferably, the outer dimensions of said replaceable cap 14 are similar or identical to the outer dimensions of a main housing component 15, which serves to accommodate the drive mechanism 10.

The drive mechanism 10 comprises a piston rod 18 having an outer thread 19 matching with an inner thread of an axially displaceable insert or lead screw 20. Moreover, the piston rod 18 is also threadedly engaged with an inner thread of an axially displaceable drive sleeve 22. Said piston rod 18 comprises a second threaded portion at its upper, proximal end section, which is not explicitly illustrated in the Figures. With its second threaded portion, it is threadedly engaged with the inner thread of the drive sleeve 22.

The piston rod 18 comprises a pressure piece 17 at its lower, hence distal, end section, which buts against a proximal end face of the piston 16 of the cartridge 8. In this way, distally directed thrust provided by the piston rod 18 is transferred to a respective distally directed movement of the piston 16, thereby expelling a pre-defined amount of the liquid medicinal product contained in the cartridge 8.

Preferably, first and second threads of the piston rod 18 are oppositely directed and comprise different leads. In this way, an axial displacement of the drive sleeve 22 leads to a rotational movement of the piston rod, which due to the threaded engagement with the insert 20 becomes also subject to a respective axial displacement in distal direction, hence, towards the lower part of the drug delivery device 4.

As illustrated in FIGS. 1 and 2, the drive mechanism 10 further comprises a dose dial sleeve 24 as well as a dose dial button 28, by means of which the drive mechanism 10 can be transferred into a configuration as illustrated in FIG. 2, wherein the drive sleeve 22 and the dose dial sleeve 24 together with the dose dial button 28 and a dose button 26 axially protrude from the housing 15 of the drive mechanism 10.

Starting from the configuration as illustrated in FIG. 2, a user may manually exert distally directed thrust to the dose button 26, which consequently leads to an axially and distally directed displacement of the entire drive mechanism 10. Due to the threaded engagement of the piston rod 18 with both, the drive sleeve 22 and the insert 20, distally directed movement of the piston rod 18 is reduced compared to the distally directed displacement of the drive sleeve 22.

Any one or several of the illustrated parts and components 12, 14, 15, 16, 17, 18, 20, 22, 24, 26, 28 may be configured as injection molded thermoplastic material having an additive embedded therein, preferably in the bulk of the thermoplastic material, which is adapted to provide a visually perceptible signal when exposed to appropriate electromagnetic radiation. In the context of the present application visually perceptible means, that the response of the additive to exposure of electromagnetic radiation is either directly visible by the human eye or can be made visible, e.g. by means of an appropriate detecting means, such as charge coupled device (CCD) cameras or other receptors, e.g. based on CMOS technology allowing for spatial resolution of detected radiation.

By means of respective image processing means, signals provided by a detector, can be made visual as required either for mass production assembly, for identification of genuine or counterfeited components and devices and/or for labelling the device and its content as being unusable for medical treatment.

In a fully automatic production of a pen-type injector as illustrated in FIGS. 1 and 2, it is typically of crucial importance to precisely determine the presence, position and/or orientation of the piston rod 18 or its pressure piece 17, which is arranged at a distal end section of the piston rod 18. In a typical assembly procedure, the drive mechanism 10 is preassembled inside the main housing component 15 and the cartridge 8 is preassembled in the cartridge holder 2. In a final assembly step, cartridge holder 2 and main housing component 15 are mutually assembled, preferably in such a way, that upon reaching of their final assembly position, the pressure piece 17 substantially gets in direct contact with the piston 16 of the cartridge 8.

For this purpose it is beneficial, if for instance the pressure piece 17 comprises a thermoplastic material having at least one additive embedded in its bulk, which is adapted to provide the visually perceptible signal when exposed to a selected spectral range of electromagnetic radiation. By contrast-enhanced visual inspection of the presence, and/or position of the pressure piece, mutual assembly of sub-assemblies, like cartridge holder 2 and main housing component 15 the mass production process can be optimized.

In a fully automated assembly process, the drive mechanism 10 is typically assembled and arranged in the main housing component 15 and forms a proximal sub-assembly. With disposable pen-injectors also the cartridge is pre-assembled in the cartridge holder 2 and forms a distal sub-assembly. Prior to a mutual assembly of proximal and distal sub-assembly, the presence, position and/or orientation of the pressure piece 17 arranged at the piston rod's 18 distal end section is visually controlled. When making use of an inspection radiation in the visible range, image acquisition has to be conducted in axial direction. Hence the long axis of the device has to be aligned substantially parallel to the optical axis of an image acquisition system.

When making use of inspection radiation in the X-ray regime, it is even possible to control the presence, position and/or orientation of the pressure piece 17 in almost any conceivable configuration and orientation of the sub-assembly with respect to the optical axis of an image acquisition system.

Additionally or alternatively not only the pressure piece 17 but also the piston 16 of the cartridge 8 may be provided with an additive featuring a comparable or similar optical response. In this way and even after termination of a final assembly, an intended abutment of piston 16 and pressure piece 17 can be optically controlled, e.g. by way of X-ray inspection.

It is of further benefit, if various illustrated components of the drug delivery device 4 comprise different additives embedded therein, respectively. In this way and by making use of an appropriate exposure to electromagnetic radiation, presence, position and/or orientation of respective components can be precisely determined by way of appropriate image acquisition and image processing.

Additionally and/or alternatively, at least one component of the illustrated drug delivery device 4 may comprise a material having an additive that provides a detectable response to electromagnetic stimulation only with respect to small spectral band of 100 nm or even below 10 nm. In this way, an effective anti-counterfeiting means can be provided, particularly, if the spectral bandwidth, at which the additive provides a detectable response, is kept secret.

LIST OF REFERENCE NUMERALS 2 cartridge holder
4 drug delivery device
8 cartridge
10 drive mechanism
12 cap
14 cap
15 housing component
16 piston
17 pressure piece
18 piston rod
19 thread
20 insert
22 drive sleeve
24 dose dial sleeve
26 dose button
28 dose dial button

The invention claimed is:

1. A drug delivery device for administering a liquid drug to a patient comprising:
a cartridge filled with the liquid drug and having a piston slidably disposed therein,
a main housing component and
a drive mechanism, wherein the drive mechanism is accommodated inside the main housing component,
wherein the drive mechanism is operably engageable with the piston of the cartridge to expel a dose of the liquid drug from the cartridge and wherein the drive mechanism comprises a piston rod with a pressure piece at a distal end section to but against a proximal end face of the piston of the cartridge;
wherein at least the pressure piece located inside the main housing component comprises a thermoplastic material having an additive embedded and homogeneously distributed in its bulk,
wherein the additive is adapted to provide a visually perceptible signal when exposed to electromagnetic radiation and
wherein the electromagnetic radiation is within one of a first spectral range, a second spectral range, or a third spectral range.

2. The drug delivery device according to claim 1, wherein the thermoplastic material comprises an injection molded thermoplastic material and wherein the additive comprises at least one dye being substantially homogeneously distributed in the material.

3. The drug delivery device according to claim 1, wherein the additive is fluorescent in response to the first spectral range of the electromagnetic radiation.

4. The drug delivery device according to claim 1, wherein the additive is photochromic with respect to the second spectral range of the electromagnetic radiation.

5. The drug delivery device according to claim 1, wherein the additive is substantially absorptive or reflective with respect to the third spectral range of the electromagnetic radiation.

6. The drug delivery device according to claim 1, wherein first, second and/or third spectral ranges have a spectral width (FWHM) of less than about 100 nm.

7. The drug delivery device according to claim 1, wherein the first, second and/or third spectral ranges are in the infrared-, visible-, UV- or X-ray spectral range.

8. The drug delivery device according to claim 1, wherein the additive irreversibly changes at least one visually perceptible property once exposed to a predetermined amount of radiation within one of the first, second and/or third spectral ranges.

9. The drug delivery device according to claim 1, wherein the drug delivery device is configured as an inhaler or an injection device.

10. The drug delivery device according to claim 9 and comprising
   a cartridge holder adapted to receive a cartridge filled with a medicinal product and having a piston slidably disposed therein,
   wherein the drive mechanism is to be operably engaged with the piston of the cartridge by way of a piston rod for dispensing of a dose of the medicinal product.

11. The drug delivery device according to claim 1, wherein the additive responds to a pre-defined spectrum of electromagnetic radiation in a different way compared to a base material of the pressure piece.

\* \* \* \* \*